(12) United States Patent
Miller et al.

(10) Patent No.: US 9,481,683 B2
(45) Date of Patent: Nov. 1, 2016

(54) 1,3-BENZOTHIAZINONE SULFOXIDE AND SULFONE COMPOUNDS

(71) Applicants: UNIVERSITY OF NOTRE DAME DU LAC, Notre Dame, IN (US); Marvin J. Miller, South Bend, IN (US); Rohit Tiwari, Silver Spring, MD (US)

(72) Inventors: Marvin J. Miller, South Bend, IN (US); Rohit Tiwari, Rockville, MD (US)

(73) Assignee: UNIVERSITY OF NOTRE DAME DU LAC, Notre Dame, IN (US)

(*) Notice: Subject to any disclaimer, the term of this patent is extended or adjusted under 35 U.S.C. 154(b) by 0 days.

(21) Appl. No.: 14/734,095

(22) Filed: Jun. 9, 2015

(65) Prior Publication Data
US 2015/0353571 A1    Dec. 10, 2015

Related U.S. Application Data

(60) Provisional application No. 62/009,641, filed on Jun. 9, 2014.

(51) Int. Cl.
*C07D 491/113*    (2006.01)
(52) U.S. Cl.
CPC .................. *C07D 491/113* (2013.01)

(58) Field of Classification Search
CPC .................................................... C07D 491/113
USPC ........................................ 544/6, 50; 514/224.2
See application file for complete search history.

(56) References Cited

U.S. PATENT DOCUMENTS

| | | | | |
|---|---|---|---|---|
| 2014/0303152 A1* | 10/2014 | Yu | ......................... | C07D 417/12 514/224.2 |
| 2015/0197529 A1* | 7/2015 | Fauber | ................. | C07D 417/10 514/210.2 |
| 2015/0353572 A1* | 12/2015 | Miller | .................. | C07D 279/08 514/151 |

\* cited by examiner

*Primary Examiner* — Kahsay Habte
(74) *Attorney, Agent, or Firm* — Neifeld IP Law, P.C.

(57) ABSTRACT

A compound, having the following formula:

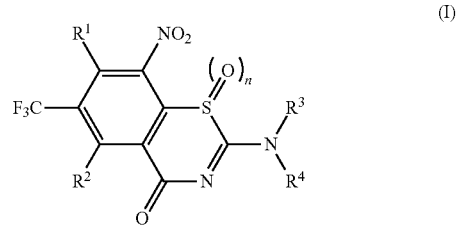

or resonance form thereof, or salt thereof, or salt of resonance form thereof is provided, wherein $R^1$-$R^4$ and n are defined herein. Compositions and methods including the compound are also provided.

13 Claims, 7 Drawing Sheets

BTZ043, 1

PBTZ169, 2

BTZ043

BTZ-SO

BTZ-SO₂

1,3-BENZOTHIAZINONE SULFOXIDE AND SULFONE COMPOUNDS

STATEMENT REGARDING FEDERALLY FUNDED RESEARCH

This invention was made with government support under grant 2R01AI054193 awarded by the National Institutes of Health (NIH). The government has certain rights in the invention.

FIELD OF THE INVENTION

This application relates to 1,3-benzothiazinone sulfoxide and 1,3-benzothiazinone sulfone compounds and compositions, methods of making, and their uses. In particular, the application relates to 1,3-benzothiazinone sulfoxide and 1,3-benzothiazinone sulfone compounds derived from BTZ043, compositions containing same, and their use, e.g., as anti-tuberculosis agents.

RELATED APPLICATIONS

This application claims priority to U.S. Provisional Application No. 62/009,641, filed 9 Jun. 2014, the entire contents of which being hereby incorporated by reference.

BACKGROUND

Tuberculosis (TB) remains a serious threat to global health. The discovery of 1,3-benzothiazin-4-ones (BTZs), especially BTZ043 and PBTZ-169 (FIG. 1) as impressively potent and selective agents for the treatment of tuberculosis (TB), prompted highly intensive research in the area of electron deficient nitroaromatic warheads as anti-TB agents.

Prior to the discovery of BTZs, several nitroaromatic compounds were found to have interesting anti-TB activity, especially PA-824, OPC67683, nitrofuranylamides and nitrofuran isooxazolines. The mode of activation of BTZ and related compounds has been shown to involve reduction of the essential nitro group to a reactive nitroso moiety 3, which then reacts with cysteine 387 of DprE1 to form a covalent, semimercaptal adduct, 4 (FIG. 2). Subsequently, several other related electron deficient aromatic compounds have been shown to cause similar covalent inhibition of DprE1, including dinitrobenzamides (e.g. DNB1), benzoquinoxalines (e.g. VI-9376) and nitrosubstituted triazoles (e.g. 377790). Recently, the present inventors' work related to the metabolic activation of BTZ043 and other nitroaromatic agents revealed that the key nitroso intermediate (i.e. 3) can also be generated by nucleophilic cine addition of thiolates or possibly hydrides. In the absence of the enzyme, azoxy and related nitroso derived dimers were generated and characterized. The present inventors also reported that further reduction produces the corresponding inactive hydroxylamine and amine. Makarov et al, recently also demonstrated that both compounds 1 and 2 undergo reduction in the presence of purified nitro reductase to the corresponding hydroxylamine and azoxy analogues. Thus, BTZ and other electrophilic nitroaromatic anti-TB compounds are susceptible to redox activation both in vitro and in vivo.

Discussions in the literature on nitroaromatic anti-TB warheads related to BTZ043 have mostly been focused on the reductive metabolism catalyzed either by DprE1 or nitroreductases. A potential alternative metabolic fate involves oxidative processes. S-Oxidation of sulfur-containing therapeutics is a well-known metabolic transformation catalyzed by cytochrome P450s or by flavin monoxygenases.

BRIEF DESCRIPTION OF THE SEVERAL EMBODIMENTS

The inventors have found, inter alia, that oxidation products, e.g., possibly metabolic oxidation products of a benzothiazinone class of nitroaromatic warheads are provided that have anti-TB activity of their own. The inventors have found that oxidation of the sulfur in benzothiazinones (BTZs) can affect the electrophilicity of the active aromatic ring of BTZ. The inventors have also found that oxidation of the BTZ sulfur alters the planar conformation of its fused ring system, and that this may influence enzyme active site recognition. In some embodiments, sulfone and sulfoxide analogs of BTZ043 are provided, which exhibit activity against non-pathogenic and pathogenic mycobacterial strains including those that cause TB. In some embodiments, the possible metabolic oxidation products include 1,3-benzothiazinone sulfoxide (BTZ-SO) and 1,3-benzothiazinone sulfone (BTZ-SO2).

One embodiment provides a compound, having the following formula:

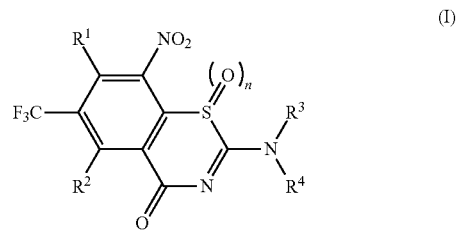

(I)

or resonance form thereof, or salt thereof, or salt of resonance form thereof;

wherein $R^1$-$R^4$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof;

wherein $R^3$ and $R^4$ may be taken together with the nitrogen to which they are attached to form a cyclic group;

wherein each group may be optionally and independently straight or branched; wherein each group may be optionally and independently substituted by one or more independent substituents; and wherein one or more than one atom in each group may be optionally and independently replaced with one or more independent heteroatoms;

and wherein n is 1 or 2.

Another embodiment provides a composition, which includes the compound and a physiologically acceptable carrier.

Another embodiment provides a method, which includes administering the compound or the composition to a subject in need thereof, to treat said subject.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from the description.

DESCRIPTION OF THE DRAWINGS

The accompanying drawings form part of the present specification and are included to further demonstrate certain embodiments, which are not intended to be limiting, of the present invention. The invention may be better understood by reference to one or more of these drawings in combination with the description of the several embodiments presented herein.

DETAILED DESCRIPTION OF THE SEVERAL EMBODIMENTS

The inventors considered that oxidation of the sulfur might affect the electrophilicity of the active aromatic ring of BTZ and possibly alter the planar conformation of its fused ring system which, in turn, might influence enzyme active site recognition, and prepared sulfone and sulfoxide analogs of the known compound BTZ043 and investigated them for anti-TB activity. Oxidized forms of BTZ043 and their activity against TB and other mycobacteria.

The Mulliken charges calculated by semi empirical AM1 method indicate that the sulfur atom of the benzothiazinone scaffold has slightly positive character. This is possibly because of the delocalization of its lone pair of electrons within the ring (see Table 1). Such delocalization affords negative character to the carbons that are adjacent to sulfur whereas the unsubstituted carbons on the central aromatic rings remain highly electron deficient. This is reflected in the dramatic downfield shift of the aromatic protons in the NMR of BTZ043 (FIG. 3) and consistent with its planarity. Consequently, it is believed that the sulfur in question is not very nucleophilic and thus, not prone to oxidation either to the sulfoxide (BTZ-SO, compound 5) or sulfone (BTZ-SO2, compound 6).

Figure 4:
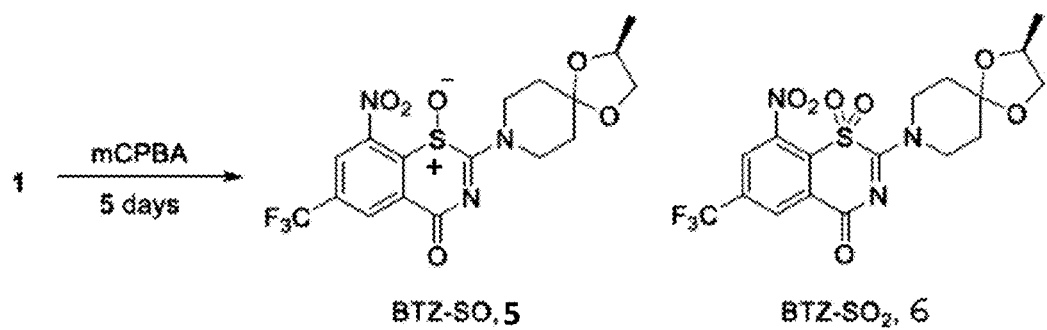
FIG. 4. Synthesis of BTZ-SO and BTZ-SO2.

Indeed, initial attempts to oxidize BTZ043 to either 5 or 6 by several reaction conditions including use of 30% H$_2$O$_2$ in glacial acetic acid at room temperature or under reflux conditions resulted in either no reaction or decomposition. Similarly treatment of BTZ043 with oxone in DCM/H$_2$O gave no reaction even after 24 h. Finally, reaction of BTZ043 with 2 eq of m-chloroperbenzoic acid (mCPBA) with BTZ043 generated small, but useable quantitites of both the sulfoxide (BTZ-SO, compound 5) in ~4% yield and sulfone (BTZ-SO2, compound 6) in ~10% yield after 5 days (FIG. 4).

Notably, BTZ043 was recovered, substantiating the diminished nucleophilicity of the BTZ sulfur as emphasized by its ionic resonance form in which the lone pair on sulfur is highly delocalized into the benzothiazinone scaffold making the sulfur resistant to oxidation.

TABLE 1

Resonance structures and calculated Mulliken charges for compounds 1, 5, and 6.

| Mulliken Charges | 1 | 5 | 6 |
|---|---|---|---|
| S1 | 0.51 | 1.55 | 2.80 |
| C2 | −0.18 | −0.44 | −0.67 |
| C3 | 0.21 | 0.18 | 0.17 |

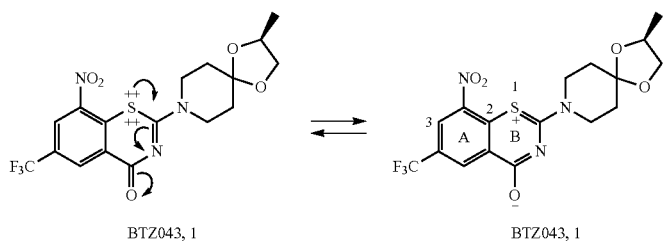

TABLE 1-continued

Resonance structures and calculated Mulliken charges for compounds 1, 5, and 6.

| Mulliken Charges | 1 | 5 | 6 |
|---|---|---|---|

5

6

<sup>a</sup>In the table, the Mulliken charges are shown only for the numbered atoms for comparison purpose. The benzothiazinone ring of 1 is divided into ring A as nitroaromatic and ring B which is a 1,4-thiazinone.

Figure 1:
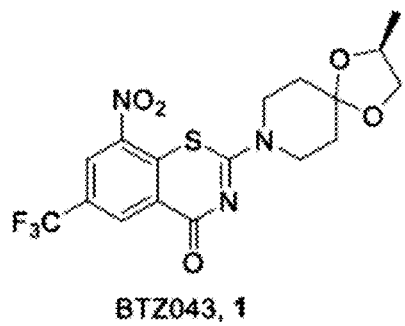
FIG. 1. Structures of known 1,3-benzothiazinone anti-TB agents, BTZ043 and PBTZ169.
Figure 1:
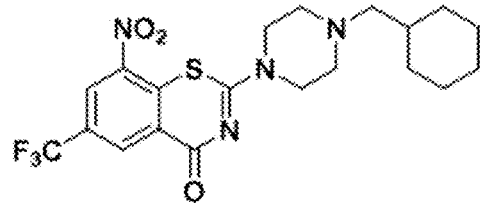
Figure 2:
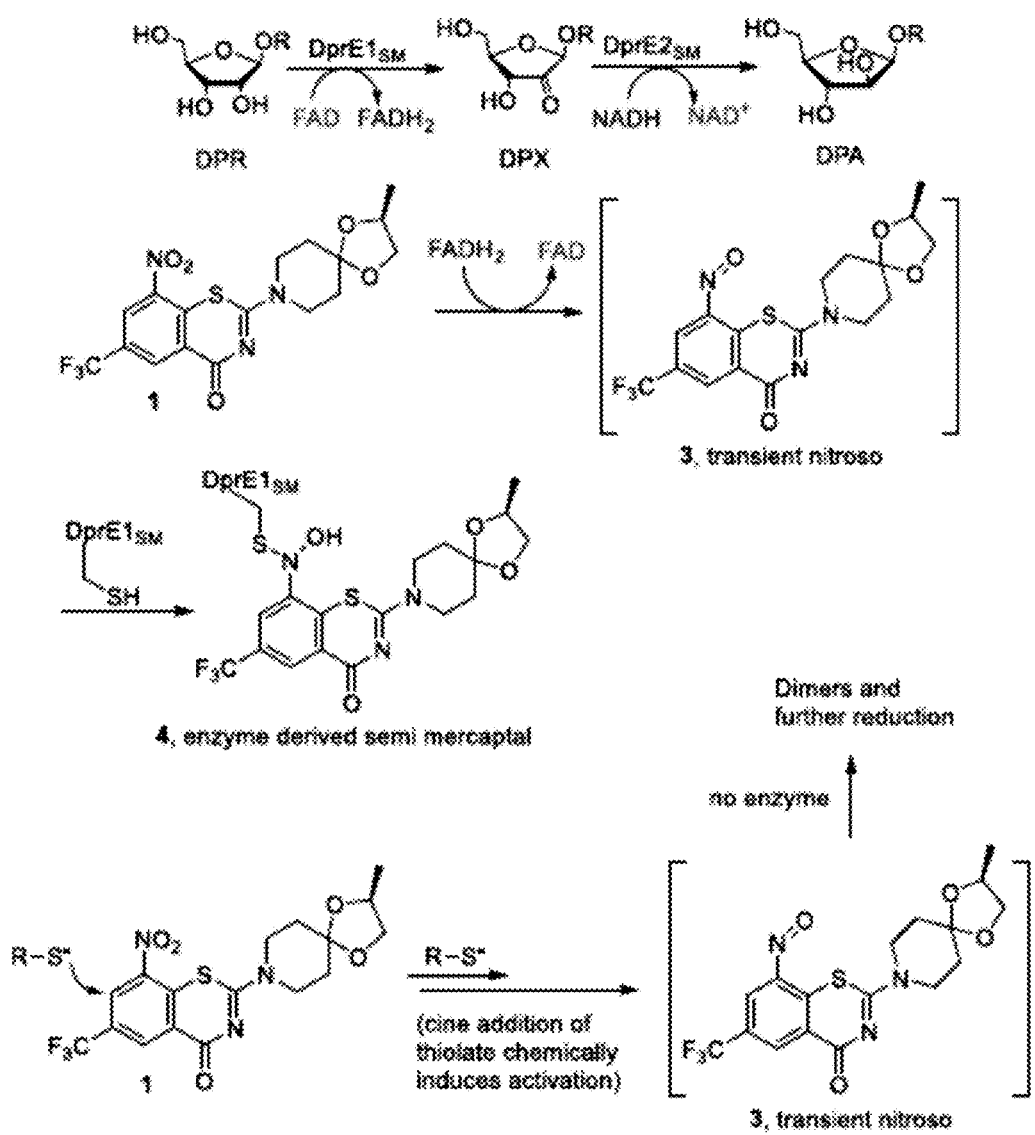
FIG. 2. Enzymatic and chemical activation of BTZ.
Figure 3:
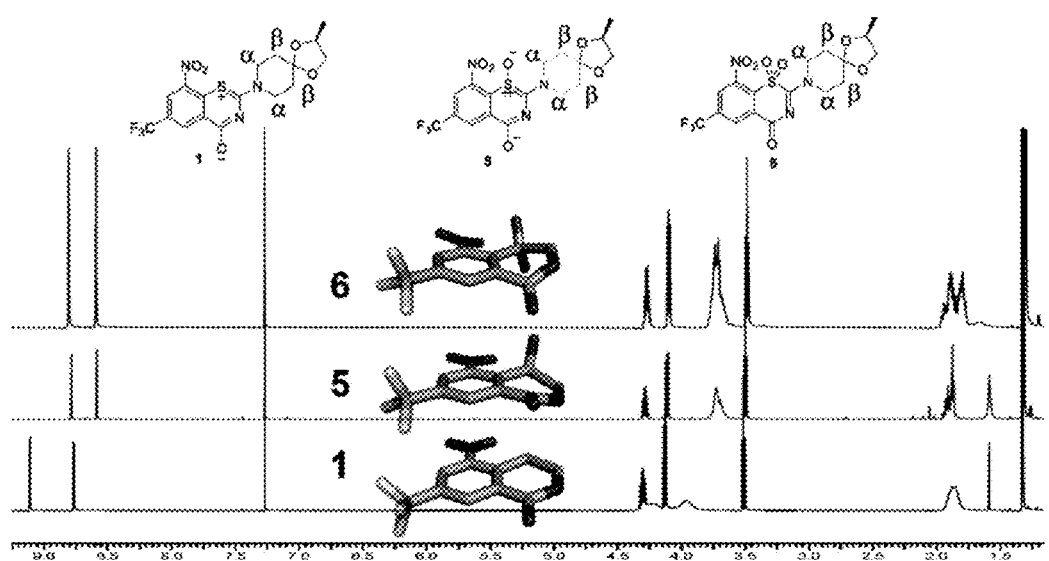
FIG. 3. The 1H NMR spectra of 1, 5 and 6. The signals of the piperidine protons α to nitrogen atom for each of 1, 5 and 6 appear in the region of 1.8-1.95 ppm whereas the signals for the protons β to the nitrogen atom appear in the 3.7-4 ppm region. The 3-dimensional pictures of benzothiazinone rings of 1, 5 and 6 are shown to explain the effect of oxidation on the thiazinone ring.

Classically, oxidation of phenyl thio ethers shifts the resonance of the aromatic protons downfield with the sulfone having a larger effect than the sulfoxide as would be expected from inductive effects. However, the actual 1H NMR spectra of 1, 5 and 6 reflect an opposite trend which is consistent with the influence of sulfur lone pair delocalization as represented by the resonance structure of 1, and to a lesser degree, sulfoxide 5. Sulfone 6 does not have such lone pair delocalization possible and can only exert an inductive effect (see Table 1). The near coincidence of the aromatic proton chemical shifts of the sulfoxide (5) and sulfone (6), illustrate the contribution of the ionic resonance form of 5 (FIG. 3 and Table 1). Less dramatic, but notable differences in the aliphatic regions of the proton NMR spectra are consistent with conformational changes due to sulfur oxidation state. Computational studies also correlate with this observation and indicate that while the bicyclic aromatic core of BTZ043 is planar, on the other hand, ring B of sulfoxide 5 and sulfone 6 are puckered and are non-aromatic. This loss of aromaticity of 1,4-thiazinone ring (ring B, see Table 1 footnote) carried out by the oxidation of 1 into 5 (1,4-thiazinone-1-oxide) and 6 (1,4-thiazinone-1,1-dioxide) may explain the poor yields of such process. Comparison of Mulliken charge calculations (Table 1) indicate differences in electrophilicity of the unsubstituted aromatic carbons (e.g. C3, Table 1) and hence, their potential susceptibility to nucleophilic attack in a related cine reaction.

Figure 5:
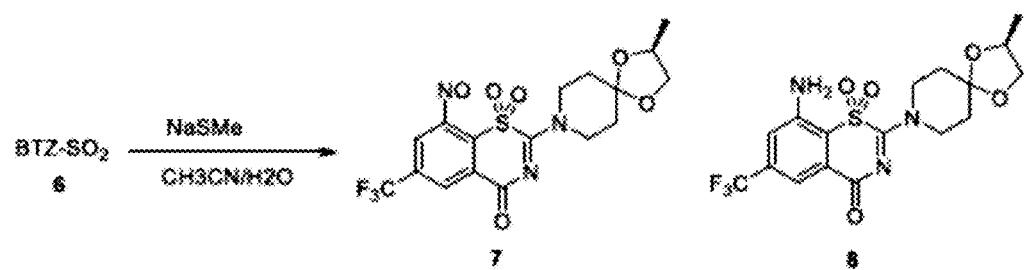
FIG. 5. Reaction of 6 with sodium methane thiolate.

Based on these NMR and computational analyses, we considered that, like BTZ043 itself, sulfoxide 5 and sulfone 6 should be prone to cine reactions with thiolates to initiate redox chemistry similar to that seen in our earlier studies with BTZ043 and related electron deficient aromatic compounds. Indeed, treatment of 6 with methane thiolate in acetonitrile/water (FIG. 5) resulted in immediate color formation reminiscent of our earlier studies with BTZ043 and other electron deficient aromatic compounds. Analysis of the reaction mixture by LC/MS revealed generation of the corresponding nitroso derivative 7 and amine 8. Extended reaction resulted in further conversion of the transient nitroso agent to the amine as expected. To confirm generation of the nitroso intermediate, the reaction was repeated in the presence of a dienes, 1,3-cyclohexadiene and α-terpinene, and, as expected, the nitroso cycloaddition products 9 or 10 were detected by LC/MS, again, just as with our earlier studies of BTZ043 and other model compounds.

Figure 6:
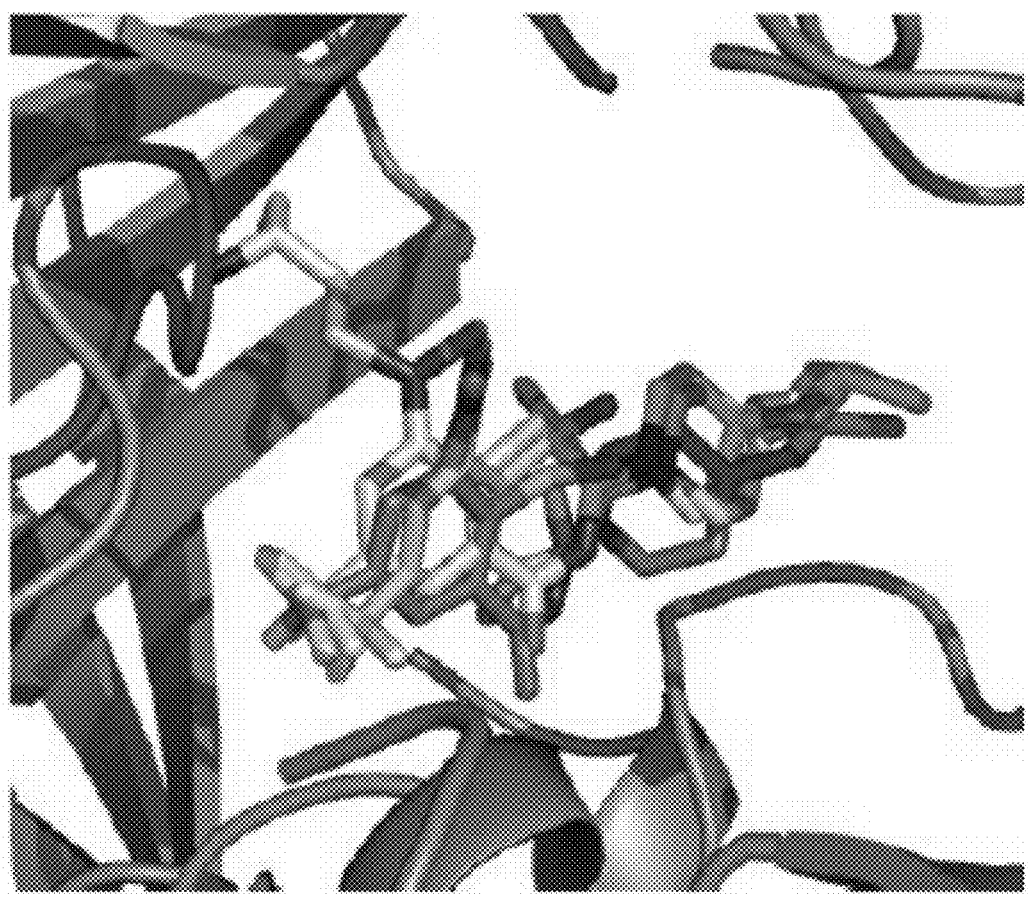
FIG. 6. Overlay of the docked poses of 5 and 6 on the sem-imercaptal adduct, 4 (carbons in white). The carbons of 5 are colored in green whereas carbons of 6 are in cyan.
Figure 7:
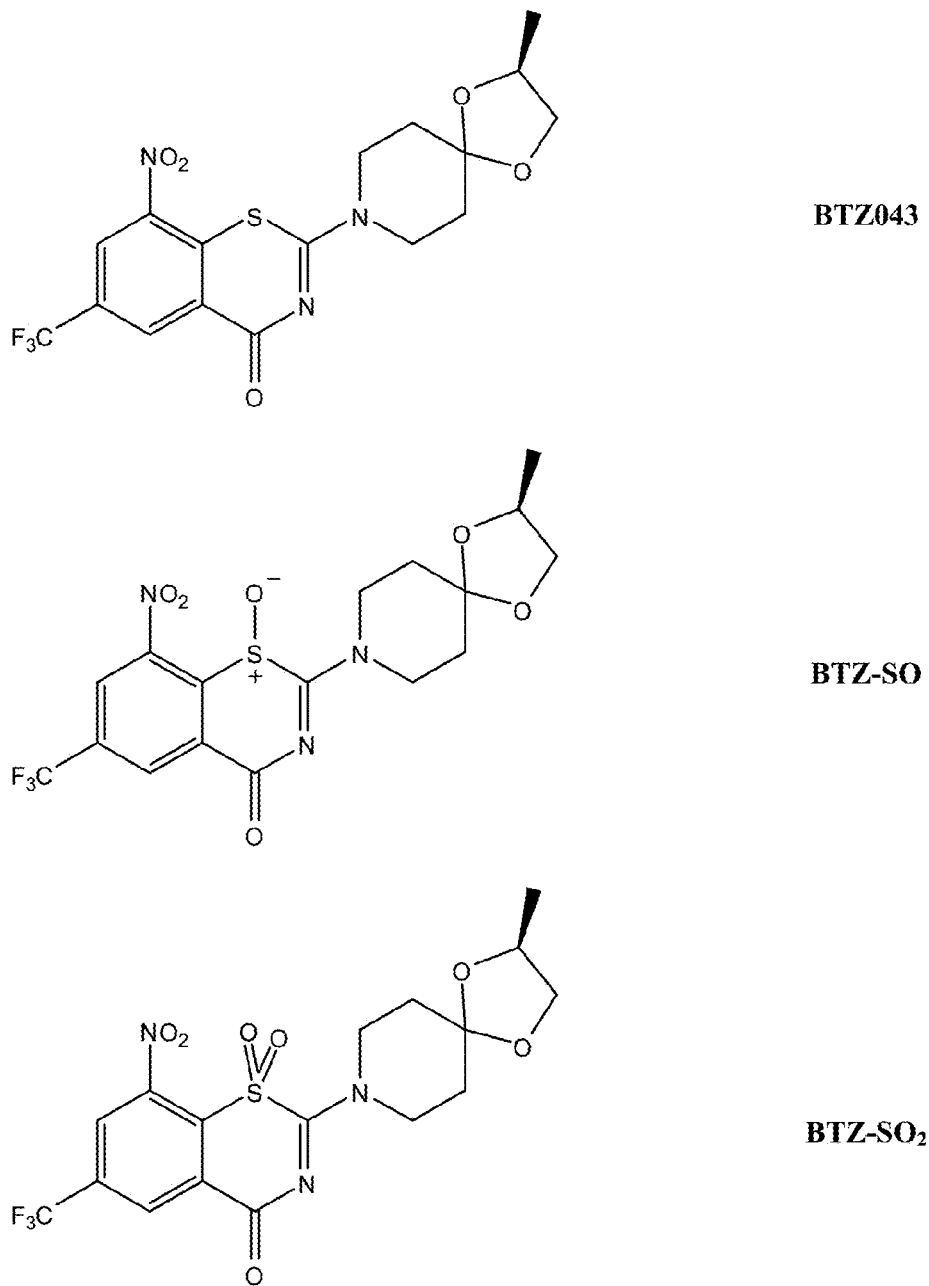
FIG. 7. Shows embodiments of BTZ043, BTZ-SO, AND BTZ-SO$_2$.

The combined NMR, computational and chemical reactivity studies suggested that sulfoxide 5 and sulfone 6 should be active anti-TB agents if they would still be recognized by the DprE1 target. Additionally, to explore the interactions of the slightly puckered 5 and puckered 6, both 5 and 6 were docked into the crystal structure of DprE1 (PDB #4F4Q) with Glide. The docking study revealed that both 5 and 6 mimicked the binding pattern of 4 in the active site of DprE1 (FIG. 6).

We were anxious to learn if the results of the chemical, NMR and computational studies would correlate with antimycobacterial activity. Both compounds 5 and 6 along with 1 were evaluated against our in-house non-pathogenic mycobacterial strains namely, M. smegmatis, M. vaccae and M. aurum. Interestingly, the sulfoxide analog, 5 showed potent activity against these strains which was comparable to that of 1; however, sulfone analog, 6 turned out to be less active as now expected based on the studies described (Table 2). Additionally we evaluated compounds 1, 5 and 6 against representative Gram positive (S. aureus, M. luteus) and Gram negative (P. aeruginosa, A. baumanii) strains. Consistent with the remarkable anti-TB selectivity of BTZ043, none of the compounds were effective inhibitors of any of these strains (Table 2).

Next, these compounds were evaluated against pathogenic mycobacterial strains namely M. tuberculosis and M. bovis (Table 3). While both of these strains cause TB, the former is causative agent in humans whereas the latter causes TB in cattle. As observed with our in-house testing in non-pathogenic mycobacteria, only the BTZ043 itself and sulfoxide analog, 5, showed impressive activity against both M. tuberculosis and M. bovis whereas the sulfone analog, 6, was only weakly active. Thus, the sulfoxide analog, 5 has activity against pathogenic and non-pathogenic strains of mycobacteria while the sulfone analog has much weaker activity.

TABLE 2

In vitro activity of the BTZ043 and related sulfur oxidation products against representative Gram positive, Gram negative and non-pathogenic mycobacterial strains.

| | M. smegmatis | M. vaccae IMET10670 | M. aurum | S. aureus SG511 | M. luteus ATCC10240 | P. aeruginosa KW799/61 | A. baumanii ATCC17961 |
|---|---|---|---|---|---|---|---|
| 1 | 0.002 | 0.002 | >200 | >0.2 | >200 | >200 | >200 |
| 5 | <0.013 | <0.013 | 3.13-12.5 | 12.5 | 50 | >200 | >200 |
| 6 | >0.5 | <0.013 | >200 | 0.2 | >200 | >200 | >200 |
| Ciprofloxacin | 0.32 | 0.32 | 0.020 | 0.32 | 1.25 | 0.156 | 0.156 |

Table 2: M. smegmatis, Mycobacterium smegamatis, M. vaccae, Mycobacterium vaccae, M. aurum, Mycobacterium aurum, S. aureus, Staphylococcus aureus, M. luteus, Mycobacterium luteus, P. aeruginosa, Pseudomonas aeruginosa, A. baumanii, Acinetobacter baumanii.

Pleased by the potent activity of the BTZ-SO (5) and weaker activity of BTZ-SO2 (6), we were interested to see if this activity trend is mimicked across other pathogenic mycobacterial strains such as M. marinum and M. kansasii which cause TB in immunocompromised individuals. Overall, the sulfoxide analog, 5 demonstrated activity against all mycobacterial strains under study and also against whereas the sulfone analog, 6 was found to be either inactive or weakly inactive against the evaluated mycobacterial strains (Table 3).

TABLE 3

In vitro activity of the BTZ043 and related sulfur oxidation products against H37Rv and other pathogenic mycobacterial strains.

| | MABA:MIC 7H12 (μM) | MABA:MIC GAS(μM) | M. marinum | M. bovis | M. kansasii |
|---|---|---|---|---|---|
| 1 | <0.02 | <0.02 | 0.037 | <0.02 | <0.02 |
| 5 | 0.06 | <0.02 | 0.19 | 0.21 | 0.30 |
| 6 | 1.46 | 0.75 | — | — | — |
| INH | 0.1 | 0.03 | >8 | 0.50 | 3.86 |
| Rifampin | 0.05 | 0.04 | 0.23 | 0.02 | 0.10 |

Table 3: Comps, Compounds; GAS, glycerol-alanine-salts medium; 7H12, 7H9 medium plus casitone, palmitic acid, albumin and catalase; MABA, Microplate Alamar Blue Assay, M. marinum, Mycobacterium marinum, M. bovis, Mycobacterium bovis, M. kansasii, Mycobacterium kansasii, VERO, African green monkey kidney cell line; LORA, low oxygen recovery assay.

The sulfur in many therapeutic agents has been known to undergo metabolic oxidation to sulfoxides and sulfones. The subtle differences in the activity of the synthesized analogs 5 and 6 will not only help predict the metabolic fate of the BTZ class of compounds but also help evaluate such compounds against various pathogenic mycobacterial strains. Therefore it was necessary for us to evaluate the cytotoxicity of 1, 5 and 6 against some representative cell lines such as PC3 (prostate cancer), MCF-7 (breast cancer) and HeLa (ovarian cancer). In general none of these compounds showed any significant cytotoxicity issues (Table 4).

TABLE 4

Cytotoxicity of 1, 5 and 6 against representative cell lines

| | PC3 | MCF-7 | HeLa |
|---|---|---|---|
| 1 | >20 | >20 | >20 |
| 5 | 15 | >20 | >20 |
| 6 | >20 | >20 | >20 |

In some embodiments, the form of the compound (I) is not particularly limiting. For example, it may be in a resonance form, a salt form, or salt of resonance form. Mixtures of different forms, and compositions that include mixtures of forms are possible.

In some embodiments, compound (I) is in the salt form. In some embodiments, compound (I) is in a resonance form. In some embodiments, the resonance form is an ionic resonance form.

In some embodiments, each $R^1$-$R^5$ group may independently and optionally be selected from one or more of the substituent groups described herein. In some embodiments, each $R^1$-$R^5$ group may independently and optionally be further substituted, and each $R^1$-$R^5$ group may independently and optionally connected directly to the relevant parent structure via one or more chemical bonds, or may be independently and optionally connected indirectly to the relevant parent structure via one or more divalent intervening substituent groups.

In some embodiments, $R^1$-$R^5$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, an alkenyl group, an alkynyl group, an aryl group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an aralkyl group, a heteroaralkyl group, oxidized form thereof, or combination thereof.

In some embodiments, $R^1$-$R^5$ are each independently hydrogen, alkyl, substituted alkyl, linear alkyl, branched alkyl, allyl, substituted allyl, heteroalkyl, cycloalkyl, aryl, substituted aryl, heteroaryl, acyl, aroyl, heteroaroyl, or combination thereof.

In some embodiments, $R^1$-$R^5$ are each independently hydrogen, alkyl, substituted alkyl allyl, substituted allyl, heteroatom substituted alkyl, cycloakyl, aryl, substituted aryl, heteratom substituted aryl, heteroaryl, acyl, aroyl, heteroaroyl, or combination thereof.

In some embodiments, $R^1$-$R^5$ are each independently hydrogen, alkyl, allyl, cycloalkyl, aryl, acyl, aroyl, or combination thereof.

In some embodiments, each $R^1$-$R^5$ group may independently and optionally be substituted, unsubstituted, saturated, unsaturated, or combination thereof.

In some embodiments, one or more than one atom in one or more of $R^1$-$R^5$ is independently replaced with one or more independent heteroatom, oxidized form thereof, or combination thereof.

In some embodiments, each $R^1$-$R^5$ group may independently and optionally have one or more atoms replaced with one or more heteroatoms, e.g., N, O, P, S, oxidized form thereof, or combination thereof.

In some embodiments, one or more than one carbon in one or more of $R^1$-$R^5$ is independently replaced with one or more independent heteroatom selected from the group consisting of N, O, S, or combination thereof.

In some embodiments, $R^3$ and $R^4$ may be taken together with the nitrogen to which they are attached to form a cyclic group.

In some embodiments, $R^3$ and $R^4$ do not form a cyclic group.

In some embodiments, wherein when the $R^3$ and $R^4$ groups are taken together with the nitrogen to form a cyclic group, the cyclic group may be suitably derived from a divalent cycloalkylene group or divalent heterocycloalkylene group. Combinations of cycloalkylene and heterocycloalkylene groups are contemplated herein. The divalent cycloalkylene and heterocycloalkylene groups may be suitably derived from the respective cycloalkyl or heterocyclic groups.

In some embodiments, the cyclic group formed from the $R^3$ and $R^4$ groups taken together with the nitrogen is an aryl group, heteroaryl group, or combination thereof. The aryl and heteroaryl group may be suitably derived from a divalent arylene group or divalent heteroarlyene group. The divalent arylene and heteroarylene groups may be suitably derived from the respective aryl or heteroaryl groups.

In some embodiments, the $R^3$ and $R^4$ cyclic group includes a 3, 4, 5, 6 membered ring or larger, which contains one or more of carbons, substituted carbons and/or heteroatoms (N, O, S) in addition to their oxidized versions, including alkenes and cycloalkenes, heterocycles and mixed carbocycle and heterocyclic moieties.

In some embodiments, $R^3$ and $R^4$ taken together with the nitrogen to which they are attached form a $C_3$-$C_{10}$ cyclic group.

In some embodiments, $R^3$ and $R^4$ taken together with the nitrogen to which they are attached form a $C_3$-$C_6$ cyclic group.

In some embodiments, $R^3$ and $R^4$ taken together with the nitrogen to which they are attached form a cycloalkene, heterocycle, mixed carbocycle and heterocycle, oxidized form thereof, or combination thereof.

In some embodiments, wherein $R^3$ and $R^4$ taken together with the nitrogen to which they are attached form a cyclic group, one or more than one carbon in the cyclic group is independently and optionally replaced with one or more heteroatom or oxidized form thereof.

In some embodiments, the group:

wherein $R^3$ and $R^4$ are taken together to form a cyclic group, may have the following cyclic structure (II):

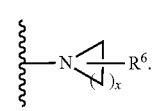

(II)

The x in the cyclic structure (II) is not particularly limiting and may have any value. In some embodiments, x is 1-10. This range includes all values and subranges therebetween, including 1, 2, 3, 4, 5, 6, 7, 8, 9, and 10.

So long as the nitrogen is present, the remaining ring portion of the cyclic structure (II) is not particularly limiting. The remaining ring portion may be suitably derived from a divalent cycloalkylene group, divalent heterocycloalkylene group, divalent arylene group, divalent heteroarlyene group, one or more of the divalent intervening substituent groups, oxidized form thereof, or combination thereof. The cyclic structure (II) may have one or more than one ring. Combinations of different are possible.

In the cyclic structure (II), one or more than one of the ring atoms may be optionally and independently replaced with one or more heteroatoms, e.g., N, O, P, S, oxidized form thereof, or combination thereof.

In the cyclic structure (II), one or more than one of the ring atoms may be optionally and independently substituted with one or more $R^6$ groups. If more than one $R^6$ group is present, they may be the same or different.

In some embodiments, each $R^6$ group may independently and optionally be selected from one or more of the substituent groups described herein.

In some embodiments, each $R^6$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, or combination thereof.

In some embodiments, each $R^6$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, an acyl group, an alkoxy group, a heterocyclic group, a heteroaryl group, a heteroarylcarbonyl group, an aryloxy group, a heteroaralkyl group, an aralkoxy group, a heteroaralkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an aralkyl group, a heteroaralkyl group, oxidized form thereof, or combination thereof.

Each $R^6$ group may independently and optionally be further substituted, and each $R^6$ group may independently and optionally connected directly to the relevant parent structure via one or more chemical bonds, or may be independently and optionally connected indirectly to the relevant parent structure via one or more divalent intervening substituent groups.

In some embodiments, $R^1$-$R^6$ are each independently an alkyl or alkenyl group. In some embodiments, the alkenyl group is an allyl group. In some embodiments, the allyl group may be linear, branched, substituted, unsubstituted, or combination thereof.

In some embodiments, the cycloalkyl may be substituted or unsubstituted, and the alkyl portion of which may be linear, branched, substituted, unsubstituted, or combination thereof.

In some embodiments, the aryl, acyl, and aroyl may be independently substituted or unsubstituted.

In some embodiments, the compound (I) has one of the following formulas:

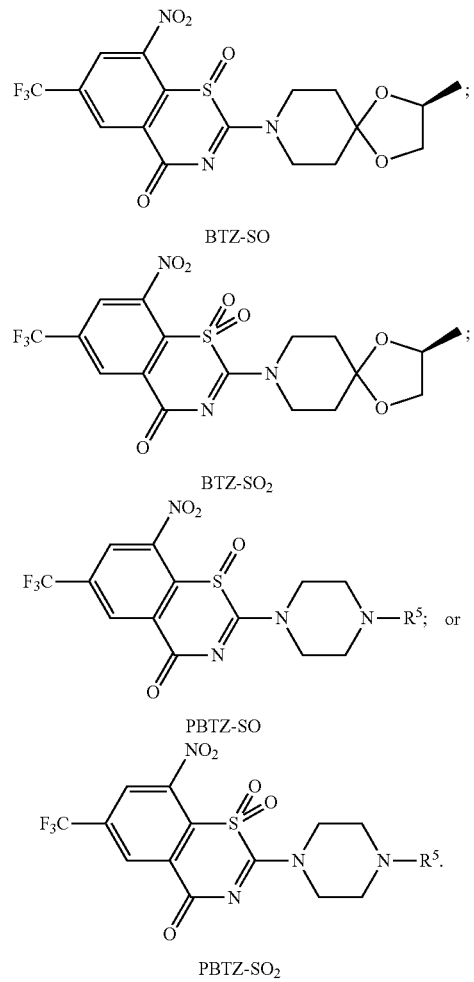

In some embodiments, $R^5$ is defined hereinabove.

In some embodiments, $R^5$ is hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, oxidized form thereof, or combination thereof.

In some embodiments, a composition is provided, which includes the compound (I) and a physiologically acceptable carrier.

In some embodiments, a method is provided, which includes administering the compound or the composition to a subject in need thereof, to treat the subject.

In some embodiments, the subject is known or suspected to need treatment for one or more maladies related to non-pathogenic mycobacterial strain, M. smegmatis, M. vaccae, M. aurum, or combination thereof.

In some embodiments, the subject is known or suspected to need treatment for one or more maladies related to Gram positive bacteria, S. aureus, M. luteus, or combination thereof.

In some embodiments, the subject is known or suspected to need treatment for one or more maladies related to Gram negative bacteria, P. aeruginosa, A. baumanii, or combination thereof.

In some embodiments, the subject is known or suspected to need treatment for one or more maladies related to pathogenic mycobacterial strain, M. tuberculosis, M. bovis, M. marinum, M. kansasaii, H37Rv, M. africanum, M. canetti, M. caprae, M. microti, M. mungi, M. pinnipedii, myobacterium tuberculosis complex, tuberculosis, or combination thereof.

In some embodiments, the subject is known or suspected to need treatment for one or more maladies related to non-pathogenic mycobacterial strain, M. smegmatis, M. vaccae, M. aurum, Gram positive bacteria, S. aureus, M. luteus, Gram negative bacteria, P. aeruginosa, A. baumanii, pathogenic mycobacterial strain, M. tuberculosis, M. bovis, M. marinum, M. kansasaii, H37Rv, M. africanum, M. canetti, M. caprae, M. microti, M. mungi, M pinnipedii, myobacterium tuberculosis complex, tuberculosis, or combination thereof.

In some embodiments, e.g., in the case of TB, the compound may be administered to a subject in need thereof together with or in addition to one or more of Isoniazid, Rifampin, Rifadin, Rimactane, Ethambutol, Myambutol, Pyrazinamide, antibiotic, fluoroquinolone, Amikacin, Kanamycin, Capreomycin, Bedaquiline, Delamanid, PA-824, Linezolid, Sutezolid, or any combination thereof.

In some embodiments, the subject is mammalian, human, livestock, cow, pig, horse, or the like. In some embodiments, a method is provided, which includes killing or inhibiting the growth of a population of one or more of non-pathogenic mycobacterial strain, M. smegmatis, M. vaccae, M. aurum, Gram positive bacteria, S. aureus, M. luteus, Gram negative bacteria, P. aeruginosa, A. baumanii, pathogenic mycobacterial strain, M. tuberculosis, M. bovis, M. marinum, M. kansasaii, H37Rv, M. africanum, M. canetti, M. caprae, M. microti, M. mungi, M. pinnipedii, myobacterium tuberculosis complex, tuberculosis, or combination thereof, by contacting one or more member of said population with the compound or composition.

In some embodiments, the population is present on a surface, and the compound or composition is contacted with said surface.

In some embodiments, an alkyl group is a univalent, acyclic, straight or branched, substituted or unsubstituted, saturated or unsaturated, hydrocarbon radical. In some embodiments, the alkyl group has the general formula (notwithstanding optional unsaturation, substitution or the like) —$C_nH_{2n+1}$. In some embodiments, n is 1-20 ($(C_1-C_{20})$ alkyl), which may suitably include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl groups. In some embodiments, the alkyl group may be straight or branched, substituted or unsubstituted, saturated or unsaturated, or any combination thereof. In some embodiments, one or more hydrogens may be optionally and independently replaced by one or more substituent groups. In some embodiments, one or more carbon atoms may be optionally and independently replaced with one or more heteroatoms such as O, S, N, B, or any combination thereof. In some embodiments, the alkyl group may contain one or more double bond, one or more triple bond, or any combination thereof. In some embodiments, the alkyl group is attached to the parent structure through one or more independent divalent intervening substituent groups. Some examples of alkyl groups, which are not intended to be limiting, include methyl, ethyl, n-propyl, isopropyl, n-butyl, iso-butyl, secondary-butyl, tertiary-butyl, and the like.

In some embodiments, a cycloalkyl group is a univalent, mono- or polycyclic, substituted or unsubstituted, saturated or unsaturated hydrocarbon radical. In some embodiments, the cycloalkyl group has the general formula (notwithstanding optional unsaturation, substitution, or the like) —$C_nH_{2n-1}$. In some embodiments, n is 3-20 ($(C_3-C_{20})$ cycloalkyl), which may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cycloalkyl groups. In some embodiments, the cycloalkyl group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the cycloalkyl group may have one or more sites of unsaturation, e.g., it may contain one or more double bond, one or more triple bond, or any combination thereof to form a cycloalkenyl or cycloalkynyl group, or combination thereof. In some embodiments, one or more carbon atoms may be optionally and independently replaced with one or more heteroatoms such as O, S, N, B, or any combination thereof. In some embodiments, the cycloalkyl group is attached to the parent structure through one or more independent divalent intervening substituent groups. Some examples of cycloalkyl groups, which are not intended to be limiting, include cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, and the like. In the case of polycyclic groups, one or more of the rings may be tethered together via bond or other divalent intervening substituent group, fused (e.g., in which one or more rings shares two or more carbon atoms or heteroatoms, joined via a single atom (e.g., spiro compound), or bridged.

In some embodiments, an alkenyl group is a univalent, straight or branched, substituted or unsubstituted, unsaturated hydrocarbon radical. In some embodiments, the alkenyl group has the general formula (notwithstanding optional substitution, higher degree of unsaturation, or the like) —$C_nH_{2n-2}$. In some embodiments, n is 2-20 ($(C_2-C_{20})$ alkenyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkenyl groups. In some embodiments, the alkenyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkenyl group is attached to the parent structure through one or more independent divalent intervening substituent groups. Some examples of alkenyl groups, which are not intended to be limiting, include ethenyl, 1-propenyl, 2-propenyl(allyl), isopropenyl, 2-methyl-1-propenyl, 1-butenyl, 2-butenyl, alkadienes, alkatrienes, and the like.

In some embodiments, an alkynyl group is a univalent, straight or branched, substituted or unsubstituted, hydrocarbon radical that contains one or more carbon-carbon triple bond. In some embodiments, the alkenyl group has the general formula (notwithstanding optional substitution, higher degree of unsaturation, or the like) —$C_nH_{2n-3}$. In some embodiments, n is 2-20 (($C_2$-$C_{20}$) alkynyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkynyl groups. In some embodiments, the alkynyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkynyl group is attached to the parent structure through one or more independent divalent intervening substituent groups. Some examples of alkynyl groups, which are not intended to be limiting, include alkadiynes, alkatriynes, ethynyl, propynyl, butyryl, and the like.

In some embodiments, an aryl group is a univalent, substituted or unsubstituted, monocyclic or polycyclic aromatic hydrocarbon radical. In some embodiments, an aryl group is a radical which, in accordance with Hückel's theory, includes a cyclic, delocalized (4n+2) pi-electron system. In some embodiments the aryl group is a $C_5$-$C_{20}$ aryl group. The $C_5$-$C_{20}$ aryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups. In some embodiments, the aryl group may be substituted or unsubstituted, be substituted with two or more groups that taken together form a cyclic group, or any combination thereof. In some embodiments, the aryl group is attached to the parent structure through one or more independent divalent intervening substituent groups. Some examples of aryl groups, which are not intended to be limiting, include phenyl, naphthyl, tetrahydronaphthyl, phenanthryl, pyrenyl, anthryl, indanyl, chrysyl, and the like.

In some embodiments, a heterocyclic group is a univalent, substituted or unsubstituted, saturated or unsaturated, mono- or polycyclic hydrocarbon radical that contains one or more heteroatoms in one or more of the rings. In some embodiments, the heterocyclic group is a $C_3$-$C_{20}$ cyclic group, in which one or more ring carbons is independently replaced with one or more heteroatoms. The $C_3$-$C_{20}$ heterocyclic group may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cyclic groups in which one or more ring carbons is independently replaced with one or more heteroatoms. In some embodiments, the heteroatoms are selected from one or more of N, O, or S, or any combination thereof. In some embodiments, the N or S or both may be independently substituted with one or more substituents. In some embodiments, the heterocyclic group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the heterocyclic group may include one or more carbon-carbon double bonds, carbon-carbon triple bonds, carbon-nitrogen double bonds, or any combination thereof. In some embodiments, the heterocyclic group is attached to the parent structure through one or more independent divalent intervening substituent groups. Some examples of heterocyclic groups, which are not intended to be limiting, include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl, and the like In some embodiments, a heteroaryl group is univalent, substituted or unsubstituted, monocyclic or polycyclic aromatic hydrocarbon radical in which one or more ring carbons is independently replaced with one or more heteroatoms selected from O, S and N. In some embodiments, in addition to said heteroatom, the heteroaryl group may optionally have up to 1, 2, 3, or 4 N atoms in the ring. In some embodiments, the heteroaryl group is an aryl group in which one or more ring carbons are independently replaced with one or more heteroatoms. In some embodiments, a heteroaryl group is an aromatic radical, which contains one or more heteroatoms and which, in accordance with Hückel's theory, includes a cyclic, delocalized (4n+2) pi-electron system. In some embodiments, the heteroaryl group is a $C_5$-$C_{20}$ heteroaryl group. The $C_5$-$C_{20}$ heteroaryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups in which one or more than one ring carbon is independently replaced with one or more heteroatoms. In some embodiments, the heteroaryl group may be substituted or unsubstituted, be substituted with two or more groups that taken together form a cyclic group, or any combination thereof. In some embodiments, the heteroaryl group is attached to the parent structure through one or more independent divalent intervening substituent groups. Some examples of heteroaryl groups, which are not intended to be limiting, include heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like.

In some embodiments, an aralkyl group is a univalent radical derived from one or more aryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of aryl group and alkyl, cycloalkyl, alkenyl, or alkynyl group is contemplated. In some embodiments, the aryl group is attached to the parent structure through one or more of the alkylene group, cycloalkylene group, alkenylene group, alkynylene group, or combination thereof as appropriate. In some embodiments, the aralkyl group may be attached to the parent structure through one or more independent divalent intervening substituent groups.

In some embodiments, a heteroaralkyl group is a univalent radical derived from one or more heteroaryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of heteroaryl group and alkyl, cycloalkyl, alkenyl, or alkynyl group is contemplated. In some embodiments, the heteroaryl group is attached to the parent structure through one or more of the alkylene group, cycloalkylene group, alkenylene group, alkynylene group, or combination thereof as appropriate. In some embodiments, the heteroaralkyl group may be attached to the parent structure through one or more independent divalent intervening substituent groups.

In some embodiments, a halo group is a univalent halogen radical or halogen-containing substituent group, e.g., one that is or contains one or more F, Br, Cl, I, or combination thereof. As used herein, the term "halogen" or "halo" includes fluoro, chloro, bromo, or iodo, or fluoride, chloride, bromide or iodide. In some embodiments, a halogen containing substituent group may suitably include a substituent group in which one or more hydrogen atoms are independently replaced with one or more halogens. In some embodiments, the halo group may be attached to the parent structure through one or more independent divalent intervening substituent groups.

In some embodiments, a hydroxy group is a univalent hydroxyl radical (—OH) or hydroxy-containing substituent group, e.g., one that is or contains one or more —OH. As used herein the term, "hydroxy" includes an —OH group. In some embodiments, a hydroxy-containing substituent group may suitably include a substituent group in which one or more hydrogen atoms are independently replaced with one or more —OH groups. In some embodiments, the hydroxyl group may be attached to the parent structure through one or more independent divalent intervening substituent groups.

In some embodiments, an oxo group is a univalent radical that contains an oxygen atom, =O, doubly bonded to carbon or another element. In some embodiments, the oxo group suitably includes aldehydes, carboxylic acids, ketones, sulfonic acids, amides, esters, and combinations thereof. In some embodiments, the oxo group may be attached to the parent structure through one or more independent divalent intervening substituent groups.

In some embodiments, a mercapto or thiol group is a univalent —SR radical or an —SR-containing group. The R group is suitably chosen from any of the substituent groups. In some embodiments, the mercapto group may be attached to the parent structure through one or more independent divalent intervening substituent groups.

In some embodiments, an amino group is a univalent —NH$_2$ radical or an —NH$_2$-containing substituent group. In some embodiments, the amino group may be attached to the parent structure through one or more independent divalent intervening substituent groups.

In some embodiments, an alkylamino group is a univalent —NRH radical or an —NRH-containing substituent group. The R group is suitably chosen from any of the substituent groups. In some embodiments, the alkylamino group may be attached to the parent structure through one or more independent divalent intervening substituent groups.

In some embodiments, a dialkylamino group is a univalent —NRR radical or an —NRR-containing substituent group. The R groups may be the same or different and are suitably and independently chosen from any of the substituent groups. In some embodiments, the dialkylamino group may be attached to the parent structure through one or more independent divalent intervening substituent groups.

In some embodiments, an acyl or carbonyl group is a univalent radical that contains a —C(=O)R group. In some embodiments, the acyl group suitably includes aldehydes, ketones, and combinations thereof. The R group is suitably chosen from any of the substituent groups. In some embodiments, the carbonyl group may be attached to the parent structure through one or more independent divalent intervening substituent groups.

In some embodiments, a carboxylic acid group is a univalent —C(=O)OH radical or a —C(=O)OH-containing substituent group. In some embodiments, the carboxylic acid group may be attached to the parent structure through one or more independent divalent intervening substituent groups.

In some embodiments, a carboxylate group is a univalent —C(=O)O$^-$ anion, —C(=O)OR, or —C(=O)OM, wherein M is a metal cation, or —C(=O)O$^-$ anion, —C(=O)OR, or —C(=O)OM-containing substituent group. The R group is suitably chosen from any of the substituent groups. The metal cation is suitably chosen from Li, Na, K, and the like. In some embodiments, the carboxylate group may be attached to the parent structure through one or more independent divalent intervening substituent groups.

In some embodiments, an amidine group is a univalent —C(=NR)NRR radical or a —C(=NR)NRR-containing substituent group. The R groups may be the same or different and are suitably and independently chosen from any of the substituent groups. In some embodiments, the amidine group may be attached to the parent structure through one or more independent divalent intervening substituent groups.

In some embodiments, an amide group is a univalent -E(=O)NRR radical or a -E(=O)NRR-containing substituent group, in which E may be other than carbon, e.g., a chalcogen (e.g., S, Se, Te), or P. In some embodiments, the amide group suitably includes univalent lactams, peptides, phosphoramides, or sulfamides, —S(=O)$_2$NRR, —P(=O)(OH)NRR, and the like. The R groups may be the same or different and are suitably and independently chosen from any of the substituent groups. In some embodiments, the amide group may be attached to the parent structure through one or more independent divalent intervening substituent groups.

In some embodiments, a carbamoyl group is a univalent —C(=O)NRR radical or a —C(=O)NRR-containing substituent group. The R groups may be the same or different and are suitably and independently chosen from any of the substituent groups. In some embodiments, the carbamoyl group may be attached to the parent structure through one or more independent divalent intervening substituent groups.

In some embodiments, a sulfonyl group is a univalent —S(=O)$_2$R radical or a —S(=O)$_2$R-containing substituent group. The R group is suitably chosen from any of the substituent groups. In some embodiments, the sulfonyl group may be attached to the parent structure through one or more independent divalent intervening substituent groups.

In some embodiments, an alkylthio or sulfide group is a univalent —SR radical or an —SR-containing substituent group. The R group is suitably chosen from any of the substituent groups. In some embodiments, the alkylthio group may be attached to the parent structure through one or more independent divalent intervening substituent groups.

In some embodiments, an alkoxy group is a univalent radical derived from an —O-alkyl group. In some embodiments, the alkylthio group may be attached to the parent structure through one or more independent divalent intervening substituent groups.

In some embodiments, an aryloxy group is a univalent radical derived from an —O-aryl group. In some embodiments, the aryloxy group may be attached to the parent structure through one or more independent divalent intervening substituent groups.

In some embodiments, a heteroaryloxy group is a univalent radical derived from an —O-heteroaryl group. In some embodiments, the heteroaryloxy group may be attached to the parent structure through one or more independent divalent intervening substituent groups.

In some embodiments, an aralkoxy group is a univalent radical derived from an —O-aralkyl group. In some embodiments, the aralkoxy group may be attached to the parent structure through one or more independent divalent intervening substituent groups.

In some embodiments, a heteroaralkoxy group is a univalent radical derived from an —O-heteroaryl group. In some embodiments, the heteroaralkoxy group may be attached to the parent structure through one or more independent divalent intervening substituent groups.

In some embodiments, an alkylcarbonyl group is a univalent is radical derived from a -carbonyl-alkyl group. In some embodiments, the alkylcarbonyl group may be attached to the parent structure through one or more independent divalent intervening substituent groups.

In some embodiments, an alkoxycarbonyl group is a univalent radical derived from a -carbonyl-O-alkyl group. In some embodiments, the alkoxycarbonyl group may be attached to the parent structure through one or more independent divalent intervening substituent groups.

In some embodiments, an alkylaminocarbonyl group is a univalent radical derived from a -carbonyl-alkylamino group. In some embodiments, the heteroaralkoxy group may be attached to the parent structure through one or more independent divalent intervening substituent groups.

In some embodiments, a dialkylamino carbonyl group is a univalent radical derived from a -carbonyl-dialkylamino group. In some embodiments, the dialkylamino carbonyl group may be attached to the parent structure through one or more independent divalent intervening substituent groups.

In some embodiments, an arylcarbonyl group is a univalent radical derived from a -carbonyl-aryl group. In some embodiments, the arylcarbonyl group may be attached to the parent structure through one or more independent divalent intervening substituent groups.

In some embodiments, a heteroarylcarbonyl group is a univalent radical derived from a -carbonyl-heteroaryl group. In some embodiments, the heteroarylcarbonyl group may be attached to the parent structure through one or more independent divalent intervening substituent groups.

In some embodiments, an aryloxycarbonyl group is a univalent radical derived from a -carbonyl-O-aryl group. In some embodiments, the aryloxycarbonyl group may be attached to the parent structure through one or more independent divalent intervening substituent groups.

In some embodiments, an alkylsulfonyl group is a univalent radical derived from a -sulfonyl-alkyl group. In some embodiments, the alkylsulfonyl group may be attached to the parent structure through one or more independent divalent intervening substituent groups.

In some embodiments, an arylsulfonyl group is a univalent radical derived from a -sulfonyl-aryl group. In some embodiments, the arylsulfonyl group may be attached to the parent structure through one or more independent divalent intervening substituent groups.

In some embodiments, a perhaloalkyl group is a univalent radical derived from a completely or substantially completely halogenated alkyl group. In some embodiments, the parhaloalkyl group may be attached to the parent structure through one or more independent divalent intervening substituent groups.

In some embodiments, a perhaloalkoxy group is a univalent radical derived from a completely or substantially completely halogenated alkoxy group. In some embodiments, the arylsulfonyl group may be attached to the parent structure through one or more independent divalent intervening substituent groups.

In some embodiments, a perhalocycloalkyl group is a univalent radical derived from a completely or substantially completely halogenated cycloalkyl group. In some embodiments, the perhalocycloalkyl group may be attached to the parent structure through one or more independent divalent intervening substituent groups.

In some embodiments, a perhaloalkenyl group is a univalent radical derived from a completely or substantially completely halogenated alkenyl group. In some embodiments, the perhaloalkenyl group may be attached to the parent structure through one or more independent divalent intervening substituent groups.

In some embodiments, a perhaloalkynyl group is a univalent radical derived from a completely or substantially completely halogenated alkynyl group. In some embodiments, the perhaloalkynyl group may be attached to the parent structure through one or more independent divalent intervening substituent groups.

In some embodiments, a perhaloaryl group is a univalent radical derived from a completely or substantially completely halogenated aryl group. In some embodiments, the perhaloaryl group may be attached to the parent structure through one or more independent divalent intervening substituent groups.

In some embodiments, a perhaloaralkyl group is a univalent radical derived from a completely or substantially completely halogenated aralkyl group. In some embodiments, the perhaloaralkyl group may be attached to the parent structure through one or more independent divalent intervening substituent groups.

In some embodiments, referring to the replacement of one or more than one atom in each group with one or more heteroatoms, the heteroatoms may be suitably chosen from N, O, P, S, B, or any combination thereof.

The substituent groups are not particularly limiting. In some embodiments, the substituent group may be suitably and independently chosen from one or more of an acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, aralkoxy group, aralkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroaralkoxy group, heteroaralkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloaralkyl group, perhaloaryl group, perhalocycloalkyl group, phosphate group, phosphine group, phospho group, sulfate group, sulfo group, sulfonyl group, oxidized form thereof, or combination thereof. Oxidized forms of the groups are possible. In some embodiments, the substituent group may be optionally and independently directly connected to the relevant parent structure via one or more chemical bonds. In some embodiments, the substituent group may be optionally and independently indirectly connected to the relevant parent structure via one or more divalent intervening substituent groups. In some embodiments, the substituent group may be optionally and independently further substituted with one or more substituent group.

The divalent intervening substituent groups are not particularly limiting. In some embodiments, the divalent intervening substituent group may be suitably and independently chosen from one or more of an azo group, azino group, azoxy group, carbonyl group, dioyl group, diazoamino group, disulfinyl group, dithio group, oxy group, hydrazo group, oxalyl group, sulfonyl group, thiocarbonyl group, thionyl group, phosphono ester group, carboxylate group, thio group; divalent residue of one or more of the following groups: acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, aralkoxy group, aralkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, heteroaralkoxy group, heteroaralkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloaralkyl group, perhaloaryl group, perhalocycloalkyl group, phosphate group, phosphine group, phospho group, sulfate group, sulfo group, sulfonyl group, oxidized form thereof, combination thereof; oxidized form thereof, or combination thereof. Oxidized forms of the groups are possible.

In some embodiments, the compound may be included in a mixture of diastereomers. If desired, the diastereomers can be separated by taking advantage of their different physical properties, such as using either recrystallization or chromatography or a combination thereof. The recrystallizations can accomplished in organic solvents such as, but not limited to, pentane, hexane, cyclohexane, toluene, benzene, chlorobutane, dichloromethane, diethyl ether, tetrahydrofuran, dimethoxyethane, acetonitrile, methanol, ethanol or butanol or a combination of organic solvents with or without water. The chromatography can be accomplished with a silica gel or alumina solid phase, eluting with mixtures of organic solvents, with or without acidic or basic modifiers, such as triethylamine, aqueous ammonia, acetic acid or aqueous hydrochloric acid.

In some embodiments, the compounds are suitable for the treatment and/or prevention of diseases and disorders characterized by mycobacterial activity or infection. The mycobacteria may be pathogenic or non-pathogenic. The mycobacteria may be Gram positive or Gram negative.

In some embodiments, the compound can be administered to a human patient by itself or in pharmaceutical compositions where it may be mixed with suitable carriers or excipients at doses to treat or ameliorate various conditions characterized by mycobacterial activity or infection. A therapeutically effective dose may refer to that amount of the compound sufficient to inhibit the mycobacterial activity or infection, it being understood that such inhibition may occur at different concentrations such that a person skilled in the art could determine the required dosage of compound to inhibit the target mycobacterial activity or infection. Therapeutically effective doses may be administered alone or as adjunctive therapy in combination with other treatments. Some examples of techniques for the formulation and administration of the compounds may be found in Remington's Pharmaceutical Sciences, 18th Edition, A. R. Gennaro, Ed., Mack Publishing Co., Easton, Pa. (1990).

Suitable routes of administration may, for example, include oral, rectal, transmucosal, buccal, intravaginal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the compound in a targeted drug delivery system, for example in a liposome.

The pharmaceutical compositions and compounds may be manufactured in a manner that is itself known, e.g., by means of conventional mixing, dissolving, dragee-making, levitating, emulsifying, encapsulating, entrapping, or lyophilizing processes. The pharmaceutical compositions thus may be formulated in conventional manner using one or more physiologically acceptable carriers comprising excipients and auxiliaries that facilitate processing of the active compounds into preparations, which can be used pharmaceutically. Proper formulation may be dependent upon the route of administration chosen.

Any combination of one or more the present compounds, salts thereof, resonance forms thereof, prodrugs, metabolites, isotopically-labeled compounds, tautomers, isomers, and/or atropisomers is possible in the composition.

For injection, the compounds may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients include but are not limited to fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as polyionic block (co)polymer, sodium carboxymethyl cellulose, sorbitol, or dextran. Optionally, the suspension may also contain suitable stabilizers or agents which increase the solubility of the compounds.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

The compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

In some embodiments, the compounds may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Non-limiting examples of pharmaceutically acceptable salts include sodium, potassium, lithium, calcium, magnesium, iron, zinc, hydrochloride, hydrobromide, hydroiodide, acetate, citrate, tartrate and maleate salts, and the like.

Generally, pharmaceutical compositions contain the active compound in an effective amount to achieve their intended purpose. In one embodiment, a therapeutically effective amount means an amount effective to prevent or inhibit development or progression of a disease characterized by mycobacterial infection or activity in the subject being treated. Determination of the effective amounts is within the capability of those skilled in the art in light of the description provided herein.

Any group described herein, whether it is expressly denoted as a "group" or is not denoted as such (e.g., using terms such as "alkyl," "aryl," "aroyl," and the like, alone) may be optionally and independently straight or branched; may be optionally and independently substituted by one or more independent substituent groups; may be optionally and independently attached directly to the relevant parent structure; may be optionally and independently attached indirectly to the relevant parent structure via one or more divalent intervening substituent groups; and/or may have one or more than one atom optionally and independently replaced with one or more independent heteroatoms.

The use of the word "a" or "an" when used in conjunction with the term "comprising" in the claims and/or the specification may mean "one," but it is also consistent with the meaning of "one or more," "at least one," and "one or more than one."

The term, "about" is used to indicate that a value includes the standard deviation of error.

The term, "or" means "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other embodiments of the invention are discussed throughout this application. Any embodiment discussed with respect to one aspect applies to other embodiments as well and vice versa. Each embodiment described herein and any obvious variation thereof is understood to be applicable to all embodiments of the invention. Given the description herein, combined with the knowledge of one of ordinary skill in the art to which the invention pertains, any embodiment described herein can be easily accomplished and/or further implemented with respect to any use, method, compound, composition, kit, obvious variant thereof, or any combination thereof.

EXAMPLES

General Experimental

All anhydrous solvents, reagent grade solvents for chromatography and starting materials were purchased from either Aldrich Chemical Co. (Milwaulkee, Wis.) or Fisher Scientific (Suwanee, Ga.). All reactions were conducted under argon unless otherwise noted. Solvents were removed in vacuo on a rotary evaporator. All compounds are >98% pure by HPLC analysis and MIC values reported are the average of three individual measurements. Water was distilled and purified through a Milli-Q water system (Millipore Corp., Bedford, Mass.). General methods of purification of compounds involved the use column chromatography with silica gel (230-400 mesh) purchased from Silicycle, Quebec city, Canada. Trimethylsilyl azide was purchased from Alfa Aesar and tert-butyl nitrite was purchased from Acros Organics. All other reagents were purchased either from Sigma Aldrich Limited or VWR. The reactions were monitored by TLC on precoated Merck 60 F254 silica gel plates and visualized using UV light (254 nm). All compounds were analyzed for purity by HPLC and characterized by 1H and 13C NMR using Bruker 400 and 500 MHz NMR spectrometers. Chemical shifts are reported in ppm ($\delta$) relative to the residual chloroform at $\delta$7.26 and coupling constants (J) are reported in hertz (Hz) (where, s=singlet, bs=broad singlet, d=doublet, dd=double doublet, dt=double of triplet, t=triplet, m=multiplet) and analyzed using 1D NMR processor (ACD/SpecManager) purchased from ACD labs (Product version 11.03). The Mass spectra values are reported as m/z and HRMS analyses were carried out with a Bruker MicroOTOF-Q II, electrospray ionization time-of-flight mass spectrometer. The semipreparative high performance liquid chromatography (HPLC) purification was performed with a Phenomenex Luna 5µ C18 column (21.20 mm×250 mm, 10 µm particle size), supplied by Phenomenex Inc. (Torrance, Calif.) using a Waters 1525 binary HPLC pump and a Waters 2489 UV/Visible detector at 280 nm wavelength. Both BTZ-SO and BTZ-SO2 were purified by an isocratic gradient formed using 80% acetonitrile and 20% 10 mM ammonium acetate at a 20 mL/min flow rate for 10 min. The liquid chromatography mass spectrum ("LC/MS") analyses were carried out on Waters ZQ instrument consisting of chromatography module Alliance HT, photodiode array detector 2996, and mass spectrometer Micromass ZQ, using a 3×50 mm Pro C18 YMC reverse phase column. Mobile phases: 10 mM ammonium acetate in HPLC grade water (A) and HPLC grade acetonitrile (B). A gradient was formed from 5% to 80% of B in 10 min at 0.7 mL/min. The MS electrospray source operated at capillary voltage 3.5 kV and a desolvation temperature 300° C.

Syntheses of BTZ-SO and BTZ-SO2: 2-((S)-2-Methyl-1,4-dioxa-8-azaspiro[4.5]decan-8-yl)-8-nitro-6-(trifluoromethyl)-4H-benzo[e][1,3]thiazin-4-one 1-oxide (5, BTZ-SO); and (S)-2-(2-Methyl-1,4-dioxa-8-azaspiro[4.5]decan-8-yl)-8-nitro-6-(trifluoromethyl)-4H-benzo[e][1,3]thiazin-4-one 1,1-dioxide (6, BTZ-SO2).

A solution of m-chloroperbenzoic acid (4 g, 23.2 mmol) in 20 mL of $CH_2Cl_2$ was added dropwise to a solution of BTZ043 (5 g, 11.6 mmol) in 25 mL of $CH_2Cl_2$ at 0° C. The resulting solution was stirred for 5 days at room temperature and washed well with two 200-mL portions of saturated $NaHCO_3$ solution and then with one 200-mL portion of water. The $CH_2Cl_2$ solution was then dried ($Na_2SO_4$), filtered and concentrated (mass recovery=6 g), and purified by column chromatography (hexanes: EtOAc, 8:2) to obtain both BTZ-SO (Rf=0.49) and BTZ-SO2 (Rf=0.36). Both of the products were subsequently purified by HPLC using the conditions already described to obtain BTZ-SO (5, 0.10 g, 2%) and BTZ-SO2 (6, 0.24 g, 4.5%).

Antibiotic Susceptibility Testing: Broth microdilution method in *M. smegmatis* (MC2155), *M. vaccae* (IMET10670), *M. aurum* (SB66), *S. aureus* (SG511), *M. luteus* (ATCC 10240), *P. aeruginosa* (KW799/61), and *A. baumanii* (ATCC17961).

Antibacterial activity of the compounds was determined by measuring their minimum inhibitory concentrations (MIC's) using the broth microdilution method according to the Clinical and Laboratory Standards Institute (CLSI, formerly the NCCLS) guidelines (*Methods for Dilution Antimicrobial Susceptibility Tests for Bacteria that Grow Aerobically*, 8th ed. (Villanova, Pa., USA), Clinical and Laboratory Standards Institute (CLSI), 2009, approved standard document M07-A7.). Each well of a 96-well microtiter plate was filled with 50 µL of sterile MHII broth. Each test compound was dissolved in DMSO making a 1 mg/mL solution, then diluted with sterile MHII broth to 40 µg/mL. Exactly 50 µL of the compound solution was added to the first well of the microtiter plate and 2-fold serial dilutions were made down each row of the plate. Exactly 50 µL of bacterial (IN BROTH) inoculum (5×105 CFU/mL) was then added to each well giving a total volume of 100 µL/well and a compound concentration gradient of 10 µg/mL-0.0049 µg/mL. The plate was incubated at 37° C. for 18-20 h and then each well was examined for bacterial growth. The MIC was recorded as the lowest compound concentration required to inhibit bacterial growth as judged by turbidity of the culture media relative to a row of wells filled with a DMSO standard. Ciprofloxacin was included in a control row at a concentration gradient of 5 µg/mL-0.0025 µg/mL.

TB (GAS and 7H12) by Microplate Alamar Blue assay (MABA): to determine MIC values against replicating TB.

The test compound MICs against Mtb H37Rv (ATCC#27294) were assessed by the MABA protocol using rifampin and INH as positive controls. Compound stock solutions were prepared in DMSO at a concentration of 128 µM, and the final test concentrations ranged from 128 µM to 0.5 µM. Two fold dilutions of compounds were prepared in glycerol-alanine-salt media in a volume of 100 µL in 96-well microplates (BD Optilux™, 96-well Microplates, black/clear flat bottom) for the GAS assay, in an iron deficient glycerol-alanine-salt media with 20% Tween 80 added in the GAST assay and in Middlebrook 7H12 medium (7H9 broth containing 0.1% w/v casitone, 5.6 µg/mL palmitic acid, 5 mg/mL bovine serum albumin, 4 mg/mL catalase) in a volume of 100 µL in 96-well microplates (BD Optilux™, 96-well Microplates, black/clear flat bottom) for the 7H12 assay. The TB cultures (100 µL inoculua of 2×105 cfu/mL) were added to the media, yielding a final testing volume of 200 µL. The plates were incubated at 37° C. On the seventh day of incubation, 12.5 µL of 20% Tween 80, and 20 µL of alamar blue (Invitrogen BioSource™) were added to the wells of test plate. After incubation at 37° C. for 16-24 h, fluorescence of the wells was measured at 530 nm (excitation) and 590 nm (emmision). The MICs are defined as the lowest concentration effecting a reduction in fluorescence of ≥90% relative to the mean of replicate bacteria-only controls.

NTM (Non-tuberculous mycobacteria) and Other Organism Assays: to determine MIC values.

For the NTM (Non-tuberculous mycobacteria) MICs, we used *M. marinum* (ATCC: 927), *M. kansasii* (ATCC:12478), and *M. bovis* BCG (ATCC: 35734). All strains were purchased from ATCC. All read outs were measured by fluorescence as exactly the same as in MABA. Culture media used for *M. bovis* BCG were in 7H12 the same as in MABA (TB assay), but all other NTMs were in Middlebrook 7H9 with OADC. Incubation temperature: *M. marinum* are at 30° C., but all other NTMs were at 37° C. Incubation times were varied as indicated below:

*M. marinum* (ATCC: 927): 5 days, and 6 h after adding resazurin dye and Tween 80. *M. kansasii* (ATCC: 12478): 6 days, and 18 h after adding resazurin dye and Tween 80. *M. bovis* BCG (ATCC: 35734): 6 days, and 18 h after adding resazurin dye and Tween 80.

Cytotoxicity Assays: against PC3, HeLa and MCF-7 cell lines.

In vitro activities against cells were determined with a crystal violet biomass reduction assay. Cells were grown in media supplemented with fetal bovin serum and penicillin/streptomycin antibiotic. 100 µL of cell inoculums was added to each well. After cell inoculation, the 96 well micro-titer plates were incubated at 37° C. and 5% $CO_2$ with 95% humidity for 24 h prior to addition of compounds. A stock solution of each compound was made in DMSO and then diluted with media to give a 40 µM solution. 100 µL of DMSO/media solutions of compounds were added in replicates of 3. 100 µL solution was added to the first set of wells. Two-fold serial dilutions were made down each row of the micro-titer plate. The cells were incubated in a 37° C., 5% $CO_2$ and 95% humidity for 72 h. The media was removed and the cells were fixed with glutaraldehyde, rinsed, stained with crystal violet, rinsed and air dried. The stain was eluted with a solution of Triton-X-100 and optical density was measured at 595 nm. Trichostatin A was used as a positive control for all the cell lines tested.

Abbreviations: DMF, N,N-dimethyl formamide; DprE1, decaprenylphosphoryl-β-D-ribose 2' oxidase; MDR, multi-drug resistant; *M. tuberculosis, Mycobacterium tuberculosis*; XDR, extensively drug resistant; TB, tuberculosis.

The work described herein surprisingly shows that the metabolic oxidation products of benzothiazinone class of nitroaromatic warheads have anti-TB activity of their own. The work further and surprisingly describes a change in the conformation brought about by the oxidations of 1 and its impact on the NMR chemical shifts of 5 and 6, which will be additionally helpful for future characterization of metabolites in the ADME/pharmacokinetics measurements.

What is claimed is:
1. A compound, having the following formula:

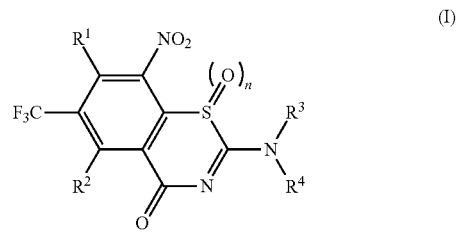

or resonance form thereof, or salt thereof, or salt of resonance form thereof;

wherein $R^1$-$R^4$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof;

wherein $R^3$ and $R^4$ may be taken together with the nitrogen to which they are attached to form a cyclic group;

wherein each group may be optionally and independently straight or branched; wherein each group may be optionally and independently substituted by one or more independent substituents; and wherein one or more than one atom in each group may be optionally and independently replaced with one or more independent heteroatoms;

wherein the one or more independent substituents is one or more of an acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, aralkoxy group, aralkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroaralkoxy group, heteroaralkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloaralkyl group, perhaloaryl group, perhalocycloalkyl group, phosphate group, phosphine group, phospho group, sulfate group, sulfo group, sulfonyl group, oxidized form thereof, or combination thereof; and wherein n is 1 or 2.

2. The compound of claim 1,
wherein $R^1$-$R^4$ are each independently hydrogen, alkyl, allyl, cycloalkyl, aryl, acyl, aroyl, or combination thereof,
said alkyl and allyl being independently linear, branched, substituted, unsubstituted, or combination thereof,
said cycloalkyl being substituted or unsubstituted, the alkyl portion of which being linear, branched, substituted, unsubstituted, or combination thereof,
said aryl, acyl, and aroyl being independently substituted or unsubstituted;
wherein $R^3$ and $R^4$ taken together with the nitrogen to which they are attached may optionally form a cyclic group, said cyclic group being substituted, unsubstituted, saturated, unsaturated, or combination thereof;
and wherein n is 1 or 2.

3. The compound of claim 1, wherein one or more than one atom in one or more of $R^1$-$R^4$ is independently replaced with one or more independent heteroatom.

4. The compound of claim 1, wherein one or more than one carbon in one or more of $R^1$-$R^4$ is independently replaced with one or more independent heteroatom selected from the group consisting of N, O, S, or combination thereof.

5. The compound of claim 1, wherein $R^1$-$R^4$ are independently hydrogen, alkyl, substituted alkyl, linear alkyl, branched alkyl, allyl, substituted allyl, heteroalkyl, cycloalkyl, aryl, substituted aryl, heteroaryl, acyl, aroyl, heteroaroyl, or combination thereof.

6. The compound of claim 1, wherein $R^3$ and $R^4$ taken together with the nitrogen to which they are attached form a $C_3$-$C_{10}$ cyclic group, said cyclic group being substituted, unsubstituted, saturated, unsaturated, or combination thereof.

7. The compound of claim 1, wherein $R^3$ and $R^4$ taken together with the nitrogen to which they are attached form a cyclic group, and wherein one or more than one carbon in the cyclic group is independently and optionally replaced with one or more heteroatom.

8. The compound of claim 1 wherein $R^3$ and $R^4$ taken together with the nitrogen to which they are attached form a $C_3$-$C_6$ cyclic group.

9. The compound of claim 1, wherein $R^3$ and $R^4$ taken together with the nitrogen to which they are attached form a cycloalkene, heterocycle, mixed carbocycle and heterocycle, oxidized form thereof, or combination thereof.

10. The compound of claim 1, having one of the following formulas:

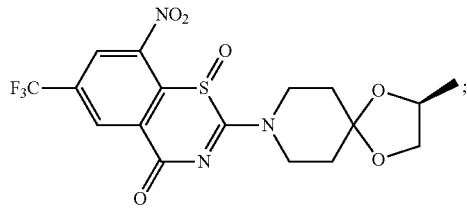

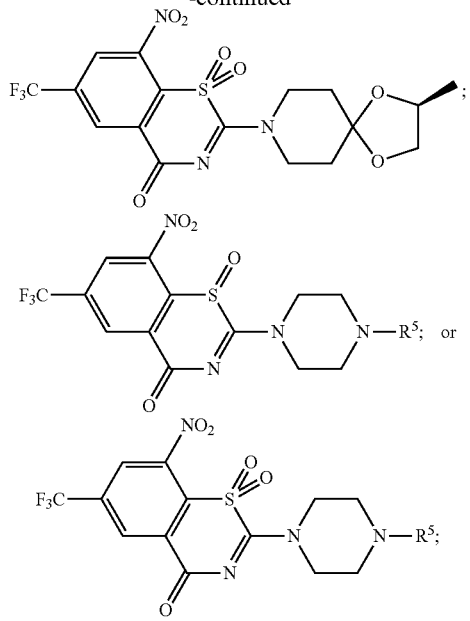

wherein $R^5$ is hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof; and
wherein each group may be optionally and independently straight or branched; wherein each group may be optionally and independently substituted by one or more independent substituents; and wherein one or more than one atom in each group may be optionally and independently replaced with one or more independent heteroatoms.

11. A composition, comprising the compound of claim 1 and a physiologically acceptable carrier.

12. A method, comprising administering the compound of claim 1 to a subject in need thereof, to treat said subject, wherein the subject is known or suspected to need treatment for one or more maladies related to non-pathogenic mycobacterial strain, *M. smegmatis*, *M. vaccae*, *M. aurum*, Gram positive bacteria, *S. aureus*, *M. luteus*, Gram negative bacteria, *P. aeruginosa*, *A. baumanii*, pathogenic mycobacterial strain, *M. tuberculosis*, *M. bovis*, *M. marinum*, *M. kansasaii*, H37Rv, *M. africanum*, *M. canetti*, *M. caprae*, *M. microti*, *M. mungi*, *M. pinnipedii*, myobacterium tuberculosis complex, tuberculosis, or combination thereof.

13. A method, comprising administering the composition of claim 11 to a subject in need thereof, to treat said subject, wherein the subject is known or suspected to need treatment for one or more maladies related to non-pathogenic mycobacterial strain, *M. smegmatis, M. vaccae, M. aurum*, Gram positive bacteria, *S. aureus, M. luteus*, Gram negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii*, myobacterium tuberculosis compl